US010022505B2

(12) United States Patent
Hu (10) Patent No.: US 10,022,505 B2
(45) Date of Patent: Jul. 17, 2018

(54) SAFETY PEN NEEDLE (71) Applicant: Promisemed Hangzhou Meditech Co., Ltd., Hangzhou, Zhejiang Province (CN)

(72) Inventor: Chaoyu Hu, Hangzhou (CN)

(73) Assignee: Promisemed Hangzhou Meditech Co., Ltd., Hangzhou, Zhejiang Province (CN)

( * ) Notice: Subject to any disclaimer, the term of this patent is extended or adjusted under 35 U.S.C. 154(b) by 0 days.

(21) Appl. No.: 15/323,354

(22) PCT Filed: Oct. 14, 2015

(86) PCT No.: PCT/CN2015/091924
§ 371 (c)(1),
(2) Date: Dec. 30, 2016

(87) PCT Pub. No.: WO2016/066014
PCT Pub. Date: May 6, 2016

(65) Prior Publication Data
US 2017/0143912 A1 May 25, 2017

(30) Foreign Application Priority Data

Oct. 29, 2014 (CN) .......................... 2014 1 0590229
Dec. 17, 2014 (CN) .......................... 2014 1 0779947

(51) Int. Cl.
*A61M 5/32* (2006.01)
*A61M 5/34* (2006.01)

(52) U.S. Cl.
CPC ........ *A61M 5/3257* (2013.01); *A61M 5/3202* (2013.01); *A61M 5/3245* (2013.01); *A61M 5/3271* (2013.01); *A61M 5/34* (2013.01)

(58) Field of Classification Search
None
See application file for complete search history.

(56) References Cited

U.S. PATENT DOCUMENTS 5,514,097 A * 5/1996 Knauer ................... A61M 5/20
604/136
5,634,910 A * 6/1997 Kanner ............. A61M 25/1018
604/208

(Continued)

FOREIGN PATENT DOCUMENTS

| CN | 103405832 A | 11/2013 |
|---|---|---|
| CN | 103458947 A | 12/2013 |

(Continued)

*Primary Examiner* — Bhisma Mehta
*Assistant Examiner* — Matthew A Engel
(74) *Attorney, Agent, or Firm* — Muncy, Geissler, Olds & Lowe, P.C.

(57) ABSTRACT

A safety insulin pen needle, including a needle hub, a needle tube assembly base arranged on the needle hub, a needle tube, a trigger protector arranged outside the needle hub and a spring arranged between the trigger protector and the needle hub. A guide groove with a special structure is arranged on the side wall of the trigger protector, and a clamping column corresponding to the guide groove is arranged on the outer edge of the side wall of the needle hub, so that the trigger protector is in a to-be-triggered state before use, and is triggered only when in use. Thus, an injection needle can be protected from being exposed to the outside after use, and cross-infection caused by mistakenly touching or reusing is avoided.

19 Claims, 4 Drawing Sheets

(56) References Cited

U.S. PATENT DOCUMENTS

| | | | | |
|---|---|---|---|---|
| 5,843,036 | A * | 12/1998 | Olive | A61M 5/2033 604/134 |
| 6,348,043 | B1 * | 2/2002 | Hagen | A61M 5/1452 604/131 |
| 6,562,006 | B1 * | 5/2003 | Hjertman | A61M 5/31553 604/208 |
| 7,553,293 | B2 * | 6/2009 | Jensen | A61M 5/326 604/110 |
| 7,695,454 | B2 * | 4/2010 | Barron | A61M 5/31541 604/187 |
| 7,771,399 | B2 * | 8/2010 | Burren | A61M 5/31553 604/207 |
| 8,276,583 | B2 * | 10/2012 | Farieta | A61M 5/2033 128/203.15 |
| 8,376,993 | B2 * | 2/2013 | Cox | A61M 5/24 604/110 |
| 9,642,973 | B2 * | 5/2017 | Karlsson | A61M 5/326 |
| 9,649,452 | B2 * | 5/2017 | Srinivasan | A61M 5/3245 |
| 2003/0093009 | A1 * | 5/2003 | Newby | A61M 5/5086 600/576 |
| 2003/0139705 | A1 | 7/2003 | Larsen et al. | |
| 2004/0019333 | A1 * | 1/2004 | Graf | A61M 5/31551 604/207 |
| 2006/0270986 | A1 * | 11/2006 | Hommann | A61M 5/2033 604/136 |
| 2007/0129686 | A1 * | 6/2007 | Daily | A61M 5/2033 604/192 |
| 2010/0016794 | A1 * | 1/2010 | Corrigan | A61M 5/2033 604/134 |
| 2010/0049125 | A1 * | 2/2010 | James | A61M 5/2033 604/110 |
| 2010/0114037 | A1 * | 5/2010 | Moser | A61M 5/20 604/210 |
| 2010/0262083 | A1 * | 10/2010 | Grunhut | A61M 5/2033 604/198 |
| 2010/0268170 | A1 * | 10/2010 | Carrel | A61M 5/2033 604/198 |
| 2011/0251553 | A1 * | 10/2011 | Ratjen | A61M 5/2033 604/89 |
| 2012/0150125 | A1 * | 6/2012 | Karlsson | A61M 5/326 604/198 |
| 2012/0283654 | A1 * | 11/2012 | MacDonald | A61M 5/24 604/211 |
| 2012/0296285 | A1 * | 11/2012 | MacDonald | A61M 5/24 604/208 |
| 2012/0296287 | A1 * | 11/2012 | Veasey | A61M 5/31511 604/211 |
| 2013/0274676 | A1 * | 10/2013 | Ekman | A61M 5/2033 604/197 |
| 2014/0012208 | A1 * | 1/2014 | Plumptre | A61M 5/31543 604/211 |
| 2014/0180216 | A1 | 6/2014 | Lin Lee et al. | |
| 2014/0288513 | A1 * | 9/2014 | Slemmen | A61M 5/3243 604/263 |
| 2015/0057637 | A1 * | 2/2015 | Herr | A61M 5/3202 604/506 |
| 2015/0073344 | A1 * | 3/2015 | Van Damme | A61M 5/2425 604/110 |
| 2015/0094666 | A1 * | 4/2015 | Bates | A61M 5/3202 604/197 |

FOREIGN PATENT DOCUMENTS

| | | |
|---|---|---|
| CN | 104307072 A | 1/2015 |
| CN | 104491955 A | 4/2015 |
| CN | 204395141 A | 6/2015 |

* cited by examiner

SAFETY PEN NEEDLE

BACKGROUND

Technical Field

The present invention relates to the field of medical devices, in particular to an insulin injection device.

Related Art

An insulin injection device, such as an insulin pen and an injection needle, as a method for treating diabetes has been widely popularized and used. Its main function is to precisely to infuse insulin into the body of a diabetic patient through the injection device, so as to achieve the purpose of controlling blood glucose of the patient.

The traditional injection needle comprises a needle hub, a needle tube and an outer protective shell. Before the traditional injection needle is used, after the protective shell is removed, the insulin injection needle is directly exposed to the outside, so that cross-infection is easily caused by mistakenly touching a needle head by accident due to no safety protection structure after use. Meanwhile, because there is no necessary protective structure, the injection needle can be reused after being used, so that there is a risk of reuse.

Based on this fact, the China utility model patent CN203315464U provides a safety insulin needle, comprising a needle hub, a needle tube and a protective device such as a self-locking seat and a needle sheath. The safety insulin needle provided by the utility model adopts a built-in safety injection needle structure; the insulin syringe needle is externally sleeved with an elastically retractable sheath, and the sheath is limited by a self-locking mechanism; after the insulin pen enters the needle hub by rotating, the self-locking mechanism can be automatically opened, and the sheath can freely and elastically move up and down to perform normal insulin injection. However, the safety insulin needle has the following disadvantages: 1. after completing the injection, the safety insulin needle cannot immediately protect the needle tip, but a protecting mechanism can protect the needle tip only after the needle tip retreats from the injection device such as the insulin pen, so that the risk of cross-infection caused by mistakenly touching still exists; 2. insulin is usually injected into a subcutaneous tissue layer instead of a muscle layer because the muscle layer absorbs quickly, and easily causes blood glucose fluctuations, so a needle head is inserted at an angle of 45 degrees in many cases during injection; however, the safety insulin injection needle provided by the utility model can only be inserted at an angle of 90 degrees when in use due to the presence of the needle sheath and other structures, so that the operation difficulty is increased and a greater risk exists in injection and even the injection cannot be completed when the needle head is relatively long or the subcutaneous tissue layer of the patient is relatively thin; 3. similarly, the needle insertion resistance is relatively great during injection also due to the presence of the needle sheath and other structures, so that the experience of the patient is relatively poor, and the operation difficulty is increased at the same time; 4. the safety insulin needle has a more complex structure and high manufacturing cost, thereby increasing the use cost of the patient, and increasing the financial burden on the patient in case of long-term use.

SUMMARY

The present invention provides a safety insulin pen needle in order to overcome the defects that the existing safety insulin injection needle is not timely in protection, inconvenient to use, relatively poor in patient experience and high in cost.

In order to solve the above-mentioned technical problems, the present invention adopts the following technical solutions:

the safety insulin pen needle comprises a needle hub and a needle tube assembly base arranged on the needle hub, a needle tube is arranged on the needle tube assembly base, the needle tube assembly base is arranged at the centre of one end of the needle hub, and an insulin pen assembly part matched with an insulin injection device is arranged at the other end of the needle hub; at least one protruding clamping column is also arranged on the outer side wall of the needle hub at an end close to the needle tube assembly base;

the safety insulin pen needle also comprises a trigger protector sleeved outside the needle hub, the trigger protector is in a sleeve shape, two ends of the trigger protector are respectively a machine end and a patient end away from the machine end, a through hole for the needle tube to pass through is formed in the patient end, at least one guide groove matched with the clamping column on the needle hub is formed in the side wall of the trigger protector, the guide groove is at least provided with one initial fixing portion and one tail end fixing portion, the initial fixing portion is close to the patient end, and the tail end fixing portion is away from the patient end; when the clamping column is positioned at the initial fixing portion, the needle tube extends out of the trigger protector through the through hole; when the clamping column is positioned at the tail end fixing portion, the needle tube is positioned in the trigger protector;

the safety insulin pen needle also comprises a spring, the spring is arranged between the needle hub and the trigger protector, and the direction of an elastic force of the spring is the same as the axis direction of the trigger protector; the clamping column on the needle hub is embedded in the guide groove in the trigger protector to movably connect the needle hub and the trigger protector.

Further, a clamping-fixing piece is arranged outside the needle hub, and the clamping-fixing piece is provided with elastic clamping jaws capable of being matched with the trigger protector; when the clamping column is positioned at the initial fixing portion, the clamping jaws are in clamping fit with the outer wall of the upper part of the machine end of the trigger protector; when the clamping column is positioned at the tail end fixing portion, the clamping jaws are positioned below the bottom of the machine end of the trigger protector or are in clamping fit with the edge of the bottom of the machine end of the trigger protector.

Further, the guide groove comprises a first guide section, a second guide section and a transition section connected between the first guide section and the second guide section, the starting end of the first guide section is the initial fixing portion, the tail end of the first guide section is connected with the starting end of the transition section, the tail end of the transition section is connected with the starting end of the second guide section, and the tail end of the second guide section is the tail end fixing portion; the starting end of the first guide section is farther away from the patient end than the tail end of the first guide section, and the tail end of the second guide section is closer to the machine end than the starting end of the second guide section.

Further, at least one of the initial fixing portion and the tail end fixing portion is provided with a unidirectional entering-exiting structure.

Further, the unidirectional entering-exiting structure is a latching mechanism or an elastic tongue piece.

Further, an annular cavity is arranged between the needle tube assembly base and the side wall of the needle hub, a downwardly extending lug boss is arranged inside the patient end of the trigger protector, one end of the spring is arranged in the annular cavity in the needle hub, and the other end of the spring is arranged on the lug boss inside the patient end of the trigger protector.

Further, an included angle between the central axis direction of the transition section of the guide groove and the axis direction of the trigger protector is not more than 45 degrees.

Further, the safety insulin pen needle also comprises a shell, the shell is in a sleeve shape, and is arranged outside the needle hub and the trigger protector, one end of the shell is closed, and the shell is internally provided with an inwardly extending sleeve for protecting the needle tube.

Further, the clamping-fixing piece is provided with a mounting base matched with the insulin pen assembly part of the needle hub, and the elastic clamping jaws are arranged on the mounting base; uniformly distributed protruded strips or embedding grooves are arranged on the outer side surface of the mounting base, and embedding openings or protruded strips matched with the protruded strips or the embedding grooves are arranged on the inner side surface of the opening end of the shell.

Further, the mounting base of the clamping-fixing piece is provided with a guide sleeve which sleeves the trigger protector in a sliding fit manner, the guide sleeve is provided with an avoidance hole, and the elastic clamping jaw is arranged in the avoidance hole. The gap between the edge of the avoidance hole and the clamping jaw is very small, so external force cannot act on the clamping jaw. When the clamping jaw is located under the bottom of the trigger protector machine end or clamps the edge of the bottom of the trigger protector machine end, the clamping jaw cannot be pulled open or prized open by external force, consequently, it is ensured that the trigger protector cannot return to the original position again, and thereby the insulin pen needle of the present invention is prevented from being used for the second time.

Further, the shell is arranged on the mounting base of the clamping-fixing piece, and is provided with opening sealing paper/film for adhering to or sealing the mounting base at the opening end.

Before the safety insulin pen needle provided by the present invention is used, the trigger protector is positioned at a place to be triggered, and the needle tube is positioned outside the trigger protector like the traditional insulin injection needle at the moment, so that the patient can freely select the injection angle according to needs, and thus the situations that the needle tube cannot be used due to the longer length of the needle tube or accidents happen due to too deep injection are avoided, and the safety insulin pen needle greatly facilitates the use of the user compared with the existing safety injection needle.

Secondly, the safety insulin pen needle provided by the invention adopts a self-trigger protecting structure, the trigger protector itself is a trigger, and is used as a needle tip protector after being triggered. The trigger protector is triggered in the use process, and immediately protects the needle tip after use, so that the defects that the existing safety needle cannot immediately protect the needle tip and needs to retreat from the injection device to protect the needle tip are overcome, and thus the risk of cross-infection caused by accidentally and mistakenly touching the needle tip after use is more effectively avoided; further, after the trigger protector is triggered to bounce, the two clamping jaws of the clamping-fixing piece are positioned below the bottom of the machine end of the trigger protector or are in clamping fit with the edge of the bottom of the machine end of the trigger protector, so that the trigger protector cannot return to the original trigger position even under the action of external force; the further design of a spring bolt structure enables the triggered trigger protector not to easily return to the initial trigger position, so that the pen needle provided by the present invention is safer after use and cannot be reused.

Thirdly, compared with the existing safety needle, the safety insulin pen needle provided by the present invention has low needle insertion resistance, reduced operation difficulty and better patient experience because the safety insulin pen needle is triggered only when in use and has no needle sheath and other structures.

According to the safety insulin pen needle provided by the present invention, the number of guide grooves on the trigger protector is preferably three, and the number of corresponding clamping columns on the outer edge of the needle hub is also three. Before the trigger protector is triggered, the first fixing position of each clamping column on the needle hub, positioned on the corresponding guide groove of the trigger protector is the initial fixing portion, and acting force applied to the trigger protector is more uniform by the design of the three clamping columns, so that the situation that the trigger protector is automatically triggered due to deflection to one side is avoided; in the use process, the trigger protector can be naturally triggered because the trigger protector easily deflects due to uniform stress through the three guide grooves; when the trigger protector bounces up after being triggered, the three guide grooves ensure that the trajectory of the trigger protector bouncing up is along the axial line direction, so that the situation that the trigger protector cannot be triggered due to friction caused by deviating from the needle hub is avoided, and meanwhile, the clamping columns favourably enter the second fixing positions, i.e., the tail end fixing portions, through the second guide sections finally.

When the safety insulin pen needle provided by the present invention is used, the opening sealing paper/film is firstly torn off, the pen needle is mounted on the insulin injection device (such as an insulin pen), the dosage for injection is set, then the shell is taken down, the needle tube is inserted into the human body for injection, and is pulled out of the injection site of the human body after the injection is completed, and the pen needle is removed and to discarded. The safety insulin pen needle has the advantages of simple structure, safety and practicability, and low manufacturing cost, not only facilitates the use of the patient, but also further reduces the financial burden on the patient.

Drawing marks are illustrated as follows: 1—needle hub, 11—needle tube assembly base, 12—needle tube, 13—clamping column, 14—insulin pen assembly part, 15—annular cavity, and 16—annular protrusion; 2—trigger protector, 21—guide groove, 22—lug boss, and 23—through hole; 201—trigger protector patient end, 202—trigger protector machine end, 211—first guide section, 212—initial fixing portion, 213—transition section, 214—second guide section, 215—tail end fixing portion, and 216—tongue piece; 3—clamping-fixing piece, 31—mounting base, 32—clamping jaw, and 33—groove; 4—spring; 5—shell, and 51—sleeve; 6—opening sealing paper.

DETAILED DESCRIPTION

Hereinafter, the present invention will be further described in detail in conjunction with the accompanying drawings and embodiments.

Refer to the accompanying drawings 1-4.

Figure 1:
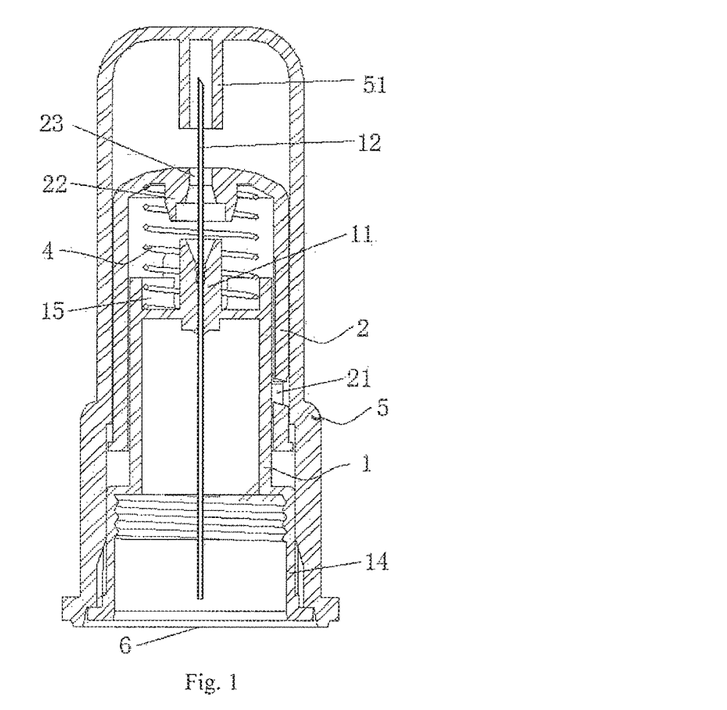
FIG. 1 is a cross-sectional view of an embodiment of a safety insulin pen needle according to the invention.
Figure 2:
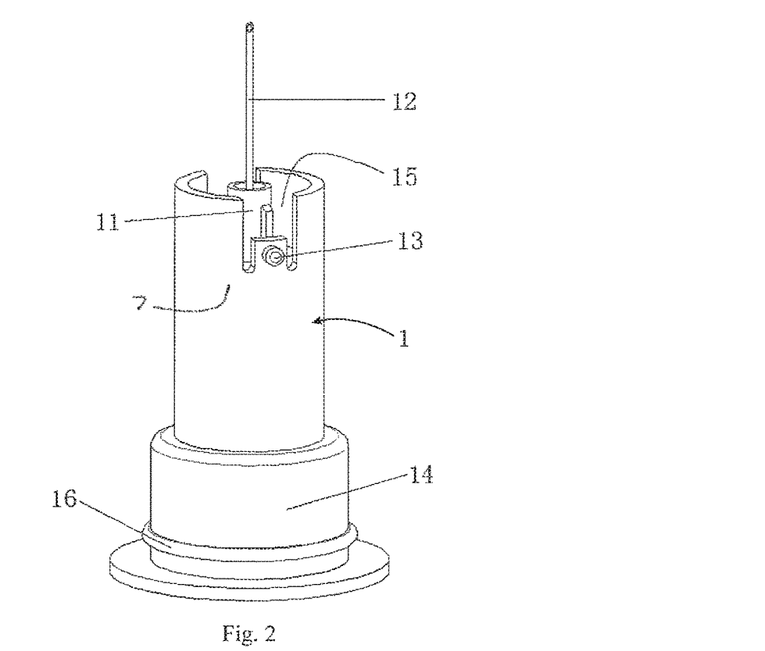
FIG. 2 is a structural schematic diagram of a needle hub in the embodiment as shown in FIG. 1.

As shown in FIG. 1, in an embodiment of the invention, a safety insulin pen needle comprises a needle hub 1. As shown in FIG. 2, an insulin pen assembly part 14 is arranged at one end of the needle hub 1, the diameter of the assembly part is greater than the rest part of the needle hub, the inner side surface of the assembly part is provided with a thread or an embedding opening configured to match with an insulin injection device (such as an insulin pen), and the outer side surface of the assembly part is provided with an annular protrusion 16 in a circle. A needle tube assembly base 11 is arranged at the centre of the other end of the needle hub 1, a needle tube 12 is arranged on the needle tube assembly base 11, and the needle tube 12 is positioned on the axial line of the needle hub 1. An annular cavity 15 is arranged between the needle tube assembly base 11 on the needle hub 1 and the side wall of the needle hub; meanwhile, at least one protruded clamping column 13 is arranged at the upper part of the outer side wall 7 of the needle hub 1; especially, in the present embodiment, the number of the clamping columns 13 is three, and the three clamping columns are uniformly distributed on the outer side wall of the needle hub at the same height.

Figure 3:
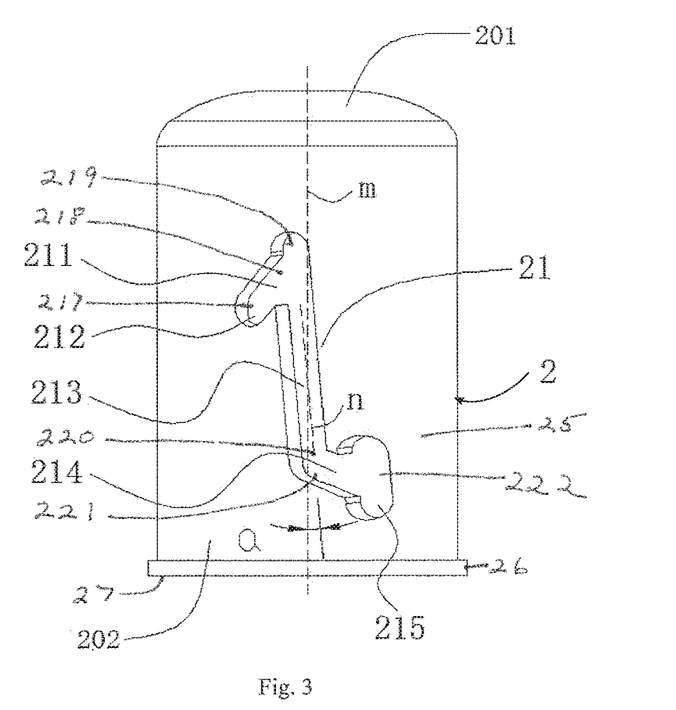
FIG. 3 is a structural schematic diagram of an embodiment of a trigger protector in the embodiment as shown in FIG. 1.

As shown in FIG. 1, according to the safety insulin pen needle in the present embodiment, the needle hub 1 is externally sleeved with a trigger protector 2 matched with the needle hub 1 in size. As shown in FIG. 3, the trigger protector 2 is in a sleeve shape, and two ends of the trigger protector 2 are respectively a machine end 202 which is open and a patient end 201 away from the machine end, a lug boss 22 extending to the machine end is arranged at the centre of the inside of the patient end 201, and a through hole 23 is formed in the centre of the lug boss for the needle tube 12 to pass through. Guide grooves 21 with the same number as the clamping columns 13 are arranged on the side wall 25 of the trigger protector 2, and the width of each guide groove is matched with the size of each clamping column 13. Each guide groove 21 comprises a first guide section 211, a second guide section 214 and a transition section 213 connected between the first guide section and the second guide section, wherein the starting end 217 of the first guide section is an initial fixing portion 212, the tail end 218 of the first guide section 211 is connected with the starting end 219 of the transition section 213, and the starting end of the first guide section is farther away from the patient end 201 than the tail end of the first guide section; the tail end 220 of the transition section 213 is connected with the starting end 221 of the second guide section 214, the tail end 222 of the second guide section is a tail end fixing portion 215, and the tail end of the second guide section is closer to the machine end 202 than the starting end of the second guide section. In order that each clamping column can smoothly slide into the tail end from the starting end in the corresponding transition section, an included angle a between the central axis n of the transition section 213 and the axis m of the trigger protector is preferably not more than 45 degrees, and a can be 0 degree.

Figure 4:
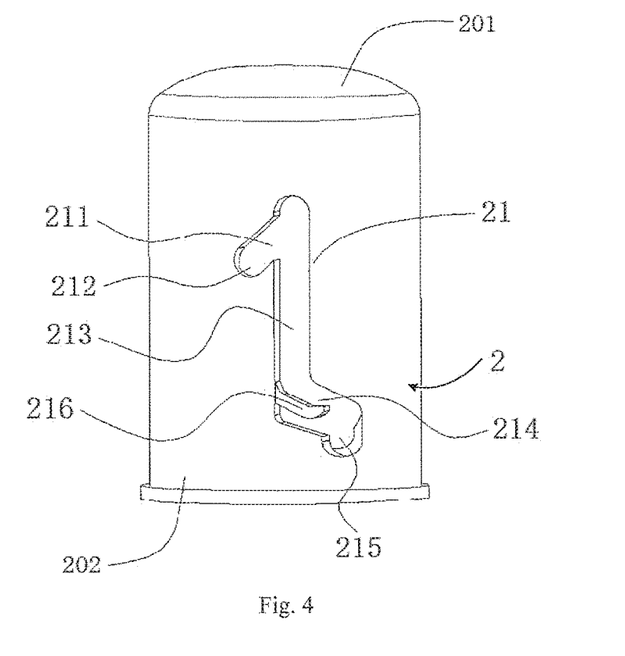
FIG. 4 is a structural schematic diagram of another embodiment of the trigger protector in the embodiment as shown in FIG. 1.

As a further improvement on the invention, as shown in FIG. 4, in another embodiment of the invention, the guide groove 21 in the trigger protector 2 is provided with a unidirectional entering-exiting structure, such as a latch or an elastic tongue piece 216 in the second guide section 214. The minimum distance between the tongue piece and the upper edge of the second guide section 214 is slightly smaller than the diameter of the clamping column 13 on the needle hub 1, so that the clamping column 13 can pass through the clearance, enter the second guide section 214 from the transition section 213 and reach the tail end fixing portion 215. When the clamping column 13 is positioned at the tail end fixing portion 215, the clamping column 13 can not be easily separated from the tail end fixing portion 215 due to the blocking of the tongue piece 216, and thus the trigger protector 2 cannot return to the initial position again.

As shown in FIG. 1, the safety insulin pen needle in the present embodiment also comprises a spring 4, and the spring 4 is arranged between the needle hub 1 and the trigger protector 2; especially, the spring 4 is stably arranged between the annular cavity 15 in the needle hub 1 and the lug boss 22 in the trigger protector 2.

As shown in FIG. 1, the safety insulin pen needle provided by the invention is further provided with a shell 5 outside the needle hub 1 and the trigger protector 2. The insulin injection needle is protected by the shell 5 before use, so that the insulin injection needle is prevented from being contaminated or being accidentally and mistakenly touched. Opening sealing paper/film 6 is further arranged at the opening end of the shell 5 to adhere to or seal the opening end, so that the needle hub 1 and the needle tube 12 inside the shell 5 are in a closed environment before use so as to avoid being contaminated by the outside.

Hereinafter, a use method of the safety insulin pen needle provided by the present invention will be described in detail. When the safety insulin pen needle is in use, the opening sealing paper/film 6 at the opening part of the shell 5 is firstly torn off, and the insulin pen assembly part 14 on the needle hub 1 is mounted on the insulin pen; then the shell 4 is removed, so that the needle tube 12 is exposed, and thus the injection is performed.

Before the injection, the safety insulin pen needle provided by the present invention is in a non-triggered state, the clamping column 13 on the outer edge of the side wall of the needle hub 1 is positioned in the initial fixing portion 212 of the guide groove 21 on the side wall of the trigger protector 2, the spring 4 is compressed at the moment, and the trigger protector 2 bears an upward elastic force of the spring; meanwhile, the starting end 217 of the first guide section is farther away from the patient end than the tail end 218 of the first guide section, so that the clamping column 13 cannot slide out of the initial fixing portion 212, thus effectively preventing the trigger protector from being falsely triggered;

the needle tube 12 extends out of the trigger protector through the through hole 23 in the patient end of the trigger protector. The safety insulin pen needle in the embodiment can be automatically triggered only in the use process, and has no additional needle sheath and other structures before use like the traditional insulin pen needle, therefore, medical staff or the patient can freely select the needle insertion angle, and the safety insulin pen needle provided by the invention is more convenient to use than the existing safety needle for that only the 90-degree needle insertion angle can be selected. Meanwhile, the better patient experience can be achieved in the injection process.

During the injection, the section, exposed out of the trigger protector 2, of the needle tube 12 is inserted into the human body, the top end of the trigger protector 2 is in contact with the human body at the moment, and the spring 4 is compressed to retract due to the acting force of the human body; meanwhile, the clamping column 13 enters the first guide section 211 from the initial fixing portion 212 of the guide groove of the trigger protector 2, and interacts with the upper edge of the first guide section 211, so that the trigger protector 2 rotates at a certain angle. When reaching the tail end of the first guide section 211, the clamping column 13 is separated from the first guide section 211 and enters the starting end 219 of the transition section 213, and then slides into the starting end of the transition section 213.

After the injection is completed, the needle tube 12 is pulled out of the human body, the trigger protector 2 bounces to the direction of the needle tube 12 under the action of the elastic force of the spring 4, and the clamping column 13 slides down along the transition section 213 and further enters the tail end fixing portion 215 through the second guide section 214. At this moment, the needle tube 12 is positioned in the trigger protector 2, so that the needle tube 12 is immediately protected, and the cross-infection caused by accidentally and mistakenly touching the used insulin injection needle exposed to the outside is avoided. Meanwhile, the to tail end of the second guide section is closer to the machine end than the starting end of the second guide section, and at this moment the trigger protector still bears the elastic force of the spring towards the patient end, so that the clamping column cannot slide out of the tail end fixing portion. In a further improvement on the present invention, the guide groove in the trigger protector is provided with an elastic tongue piece in the second guide section, so that the clamping column can be more effectively prevented from sliding out of the tail end fixing portion, and thus a needle head is prevented from being exposed out of the trigger protector.

Figure 5:
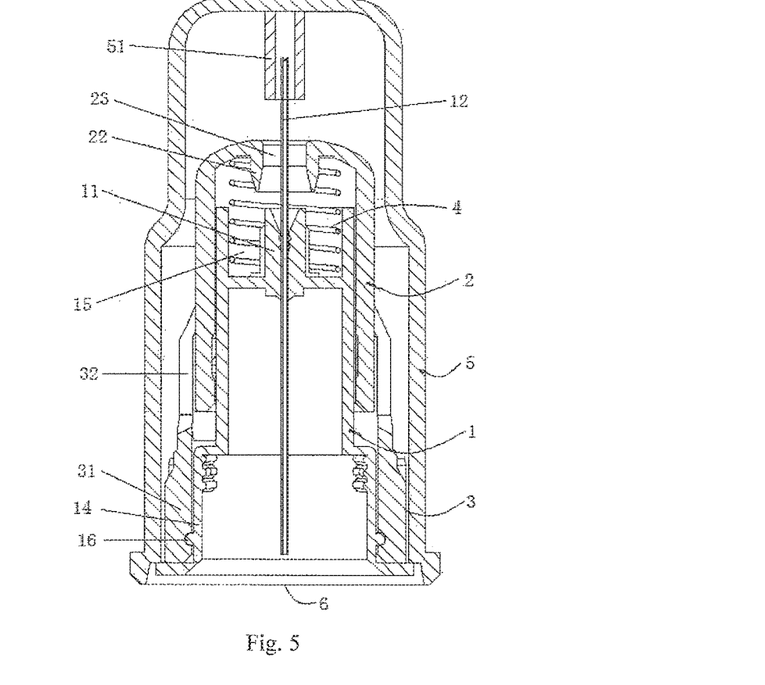
FIG. 5 is a cross-sectional view of another embodiment of the invention.
Figure 6:
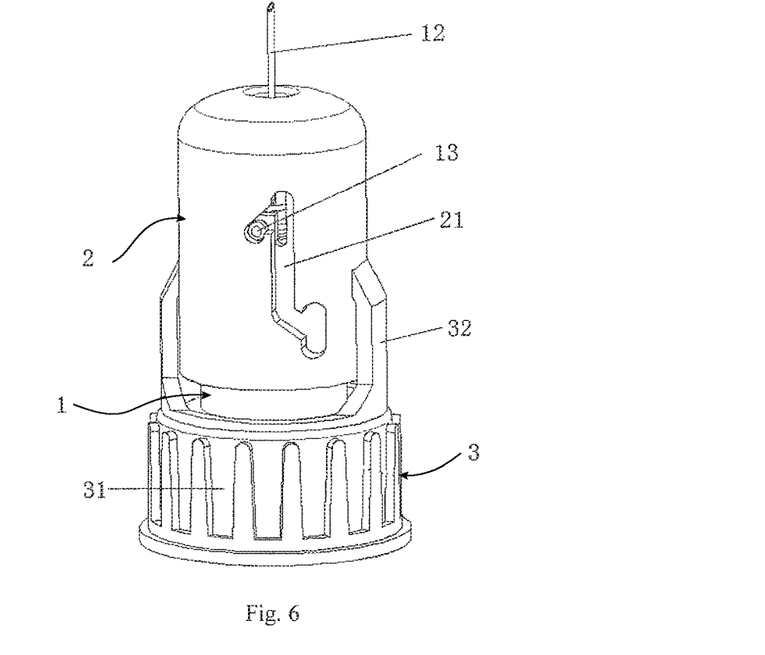
FIG. 6 is a structural schematic diagram in the embodiment as shown in FIG. 5 after a shell is removed.
Figure 7:
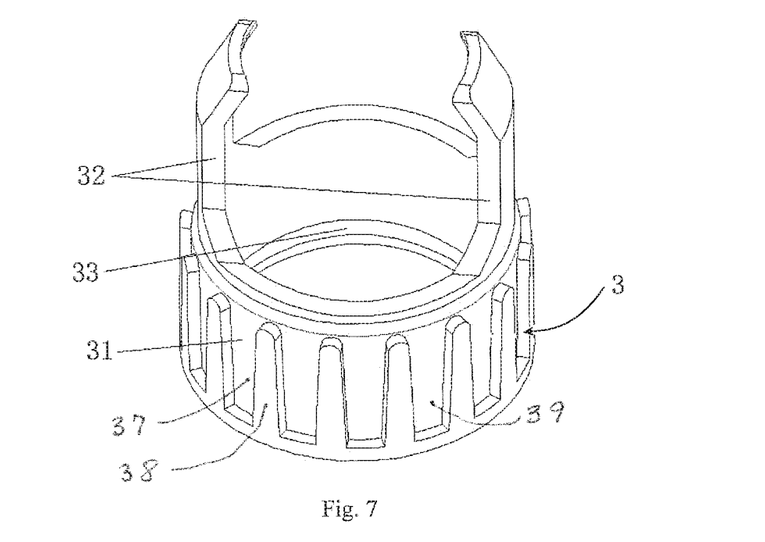
FIG. 7 is a structural schematic diagram of a clamping-fixing piece in the embodiment as shown in FIG. 5.

The technical purpose and beneficial effects of the present invention can be achieved by the embodiments of the present invention adopting the above-mentioned technical solutions. However, by considering that under special circumstances (such as human effects), after the safety insulin pen needle provided by the present invention completes the injection, the clamping columns are possibly separated from the tail end fixing portion, and even return to the initial fixing portion to be repeatedly used, a further improvement on the present invention is made by inventors. As shown in FIG. 5 and FIG. 6, the safety insulin pen needle provided by the present invention also comprises a clamping-fixing piece 3. As shown in FIG. 7, the clamping-fixing piece 3 comprises a mounting base 31 matched with the insulin pen assembly part 14 on the needle hub 1 and two elastic clamping jaws 32 extending from the mounting base 31 to the patient end 201 of the trigger protector 2, and the elastic clamping jaws 32 are in clamping fit with the outer wall of the upper part of the machine end of the trigger protector before the clamping columns fall into the tail end fixing portion. Especially, in the present embodiment, a groove 33 in a circle is formed inside the mounting base 31 of the clamping-fixing piece 3, and is configured to be matched with an annular protrusion 16 on the outer side surface of the insulin pen assembly part 14 on the needle hub 1, and the clamping-fixing piece 3 is arranged on the insulin pen assembly part 14. Further, a plurality of uniformly distributed protruded strips 38 or embedding grooves 39 are arranged on the outer side surface 37 of the mounting base 31, and embedding openings or protruded strips matched with the above-mentioned protruded strips or embedding grooves are arranged at the opening end of the shell 4, and are configured to mount the shell 4 on the clamping-fixing piece 3.

When the trigger protector 2 is in a non-triggered state, the end parts of the two clamping jaws 32 of the clamping-fixing piece 3 are positioned at the upper part of the machine end 202 of the trigger protector 2, and cling to the outer wall of the trigger protector under the action of elastic force. After the trigger protector 2 is triggered to bounce up, the lower edge of the machine end moves up, so that the end parts of the two clamping jaws 32 of the clamping-fixing piece 3 are positioned below the bottom 27 of the machine end of the trigger protector, and retract towards each other, and the distance between the end parts of the two clamping jaws is smaller than the outer diameter of the trigger protector; at this moment, the end parts of the clamping jaws are propped against the bottom of the machine end of the trigger protector, or a small section of clearance exists between the end part of each of the clamping jaws and the bottom of the machine end, but the width of each section of clearance is smaller than the distance between the needle head of the needle tube and the end part of the patient end of the trigger protector. Or in another embodiment, after the trigger protector 2 bounces up, and the machine end of the trigger protector moves up, the two clamping jaws 32 of the clamping-fixing piece 3 can be in clamping fit with the edge 26 of the bottom of the machine end of the trigger protector. The above-mentioned clamping-fixing piece is arranged, so that the trigger protector difficultly returns to the initial position again even under the action of external force, and thus the needle head cannot be exposed to the outside of the trigger protector after completing the injection, and the repeated use of the safety insulin pen needle provided by the present invention is effectively avoided.

Figure 8:
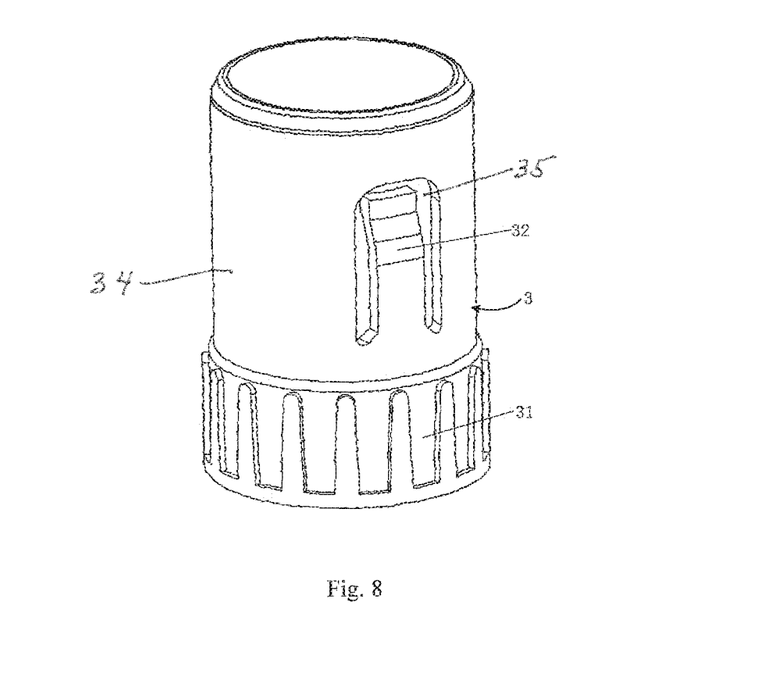
FIG. 8 is a structural schematic diagram of another embodiment of the clamping piece in the invention.

As a further improvement, as shown in FIG. 8, in another embodiment of the present invention, the mounting base 31 of the clamping-fixing piece 3 is provided with a guide sleeve 34 which sleeves the trigger protector 2 in a sliding fit manner, the guide sleeve 34 is provided with an avoidance hole 35, and the elastic clamping jaw 32 is arranged in the avoidance hole 35. In particular, the gap between the edge of the avoidance hole 35 and the clamping jaw 32 is very small, so that external force cannot act on the clamping jaw 32. When the clamping jaw 32 is located under the bottom of the trigger protector 2 machine end or clamps the edge of the bottom of the trigger protector machine end after the trigger protector 2 is triggered to spring up, the guide sleeve 34 can protect the clamping jaw 32, so that the clamping jaw 32 cannot be pulled open or pried open by external force, consequently, it is ensured that the trigger protector 2 cannot return to the original position again, and thereby the insulin pen needle of the present invention is prevented from being used for the second time.

Although the present invention has been described in detail with reference to better embodiments, it is to be finally illustrated that these embodiments are merely used to illustrate rather than limit the technical solutions of the present invention. Those skilled in the art should understand that modifications or equivalent replacements can be made to the technical solutions of the present invention without departing from the purpose and scope of the technical solutions of the present invention, and should be covered within the scope of the claims of the present invention.

What is claimed is:

1. A safety insulin pen needle, comprising a needle hub and a needle tube assembly base arranged on the needle hub, a needle tube being arranged on the needle tube assembly base, and the safety insulin pen needle comprising:
the needle tube assembly base is arranged at a center of one end of the needle hub, and an insulin pen assembly part matched with an insulin injection device is arranged at the other end of the needle hub; at least one protruding clamping column is also arranged on an outer side wall of the needle hub;
the safety insulin pen needle also comprises: a trigger protector sleeved outside the needle hub, the trigger protector is in a sleeve shape, two ends of the trigger protector are respectively a machine end and a patient end away from the machine end, a through hole for the needle tube to pass through is formed in the patient end, at least one guide groove matched with the at least one clamping column on the needle hub is formed in a side wall of the trigger protector, the at least one guide groove is at least provided with an initial fixing portion and a tail end fixing portion, the initial fixing portion is close to the patient end, and the tail end fixing portion is away from the patient end; when the at least one clamping column is positioned at the initial fixing portion, the needle tube extends out of the trigger protector through the through hole; when the at least one clamping column is positioned at the tail end fixing portion, the needle tube is positioned in the trigger protector;
the safety insulin pen needle also comprises a spring, the spring is arranged between the needle hub and the trigger protector, and the direction of elastic force of the spring is the same as the axis direction of the trigger protector; the at least one clamping column on the needle hub is embedded in the at least one guide groove in the trigger protector to movably connect the needle hub and the trigger protector;
a clamping-fixing piece is arranged outside the needle hub, and the clamping-fixing piece is provided with at least one elastic clamping jaw capable of being matched with the trigger protector; when the at least one clamping column is positioned at the initial fixing portion, the at least one clamping jaw is in clamping fit with the outer wall of an upper part of the machine end of the trigger protector; when the at least one clamping column is positioned at the tail end fixing portion, the at least one clamping jaw is positioned below a bottom of the machine end of the trigger protector or are in clamping fit with an edge of the bottom of the machine end of the trigger protector.

2. The safety insulin pen needle of claim 1, wherein the at least one guide groove comprises a first guide section, a second guide section and a transition section connected between the first guide section and the second guide section, a starting end of the first guide section is the initial fixing portion, a tail end of the first guide section is connected with a starting end of the transition section, a tail end of the transition section is connected with a starting end of the second guide section, and a tail end of the second guide section is the tail end fixing portion; the starting end of the first guide section is farther away from the patient end than the tail end of the first guide section, and the tail end of the second guide section is closer to the machine end than the starting end of the second guide section.

3. The safety insulin pen needle of claim 2, wherein an included angle between the central axis direction of the transition section of the at least one guide groove and the axis direction of the trigger protector is not more than 45 degrees.

4. The safety insulin pen needle of claim 2, wherein at least one of the initial fixing portion and the tail end fixing portion is provided with a unidirectional entering-exiting structure.

5. The safety insulin pen needle of claim 1, wherein at least one of the initial fixing portion and the tail end fixing portion is provided with a unidirectional entering-exiting structure.

6. The safety insulin pen needle of claim 5, wherein the unidirectional entering-exiting structure is a latching mechanism or an elastic tongue piece.

7. The safety insulin pen needle of claim 6, further comprising a shell, wherein the shell is in a sleeve shape, and is arranged outside the needle hub and the trigger protector, one end of the shell is closed, and the shell is internally provided with an inwardly extending sleeve for protecting the needle tube.

8. The safety insulin pen needle of claim 7, wherein the clamping-fixing piece is provided with a mounting base matched with the insulin pen assembly part of the needle hub; uniformly distributed protruded strips or embedding grooves are arranged on an outer side surface of the mounting base, and embedding openings or protruded strips matched with the protruded strips or the embedding grooves are arranged on an inner side surface of an opening end of the shell.

9. The safety insulin pen needle of claim 8, wherein the mounting base of the clamping-fixing piece is provided with a guide sleeve which sleeves the trigger protector in a sliding fit manner, the guide sleeve is provided with an avoidance hole, and one of the at least one elastic clamping jaws is arranged in the avoidance hole.

10. The safety insulin pen needle of claim 9, wherein the shell is arranged on the mounting base of the clamping-fixing piece, and is provided with opening sealing paper/film for adhering to or sealing the mounting base at the opening end of the shell.

11. The safety insulin pen needle of claim 1, wherein an annular cavity is arranged between the needle tube assembly base and the outer side wall of the needle hub, a downwardly extending lug boss is arranged inside the patient end of the trigger protector, one end of the spring is arranged in the annular cavity in the needle hub, and the other end of the spring is arranged on the lug boss inside the patient end of the trigger protector.

12. The safety insulin pen needle of claim 11, further comprising a shell, wherein the shell is in a sleeve shape, and is arranged outside the needle hub and the trigger protector, one end of the shell is closed, and the shell is internally provided with an inwardly extending sleeve for protecting the needle tube.

13. The safety insulin pen needle of claim 12, wherein the clamping-fixing piece is provided with a mounting base matched with the insulin pen assembly part of the needle hub; uniformly distributed protruded strips or embedding grooves are arranged on an outer side surface of the mounting base, and embedding openings or protruded strips matched with the protruded strips or the embedding grooves are arranged on an inner side surface of an opening end of the shell.

14. The safety insulin pen needle of claim 13, wherein the mounting base of the clamping-fixing piece is provided with a guide sleeve which sleeves the trigger protector in a sliding fit manner, the guide sleeve is provided with an avoidance hole, and one of the at least one elastic clamping jaws is arranged in the avoidance hole.

15. The safety insulin pen needle of claim 14, wherein the shell is arranged on the mounting base of the clamping-fixing piece, and is provided with opening sealing paper/film for adhering to or sealing the mounting base at the opening end of the shell.

16. The safety insulin pen needle of claim 1, further comprising a shell, wherein the shell is in a sleeve shape, and is arranged outside the needle hub and the trigger protector, one end of the shell is closed, and the shell is internally provided with an inwardly extending sleeve for protecting the needle tube.

17. The safety insulin pen needle of claim 16, wherein the clamping-fixing piece is provided with a mounting base matched with the insulin pen assembly part of the needle hub; uniformly distributed protruded strips or embedding grooves are arranged on an outer side surface of the mounting base, and embedding openings or protruded strips matched with the protruded strips or the embedding grooves are arranged on an inner side surface of an opening end of the shell.

18. The safety insulin pen needle of claim 17, wherein the mounting base of the clamping-fixing piece is provided with a guide sleeve which sleeves the trigger protector in a sliding fit manner, the guide sleeve is provided with an avoidance hole, and one of the at least one elastic clamping jaws is arranged in the avoidance hole.

19. The safety insulin pen needle of claim 18, wherein the shell is arranged on the mounting base of the clamping-fixing piece, and is provided with opening sealing paper/film for adhering to or sealing the mounting base at the opening end of the shell.

* * * * *